United States Patent [19]

Ackley

[11] Patent Number: 4,510,928
[45] Date of Patent: Apr. 16, 1985

[54] COMBINATION SLING AND THERAPY DEVICE

[76] Inventor: John B. Ackley, 430 Ridgewood Ave., Glen Ridge, N.J. 07028

[21] Appl. No.: 544,901

[22] Filed: Oct. 24, 1983

[51] Int. Cl.³ .............................................. A61F 5/40
[52] U.S. Cl. ..................................................... 128/94
[58] Field of Search ...................... 128/87 R, 89 R, 94

[56] References Cited

U.S. PATENT DOCUMENTS

| 1,304,153 | 5/1919 | Bugge | 128/94 |
| 2,306,715 | 12/1942 | Rubinstein | 128/94 |
| 3,442,267 | 5/1969 | Koygier | 128/133 |

*Primary Examiner*—John D. Yasko
*Assistant Examiner*—Christa K. Scott
*Attorney, Agent, or Firm*—Howard E. Thompson, Jr.

[57] ABSTRACT

A combination sling and therapy device is provided in the form of an elongated tubular member of pliable material, open at one end and closed at the other end, and having a slit portion extending throughout the major portion of its length incorporating adjustable fastener means whereby the tubular member can closely envelop an arm and cast assemblage from a point adjacent the fingers to at least the elbow of the user, an elongated band member having opposed ends engaging spaced portions of the tubular member, said band member being of a length to extend over the shoulder of a user and having adjustable means for providing the desired angular support for the forearm and cast, the closed end of said tubular member having a puppet-like characterization in which protruding movable lip portions are positioned to receive the thumb and fingers of the user, and at least for encouraging periodic manipulation of the thumb and fingers.

15 Claims, 9 Drawing Figures

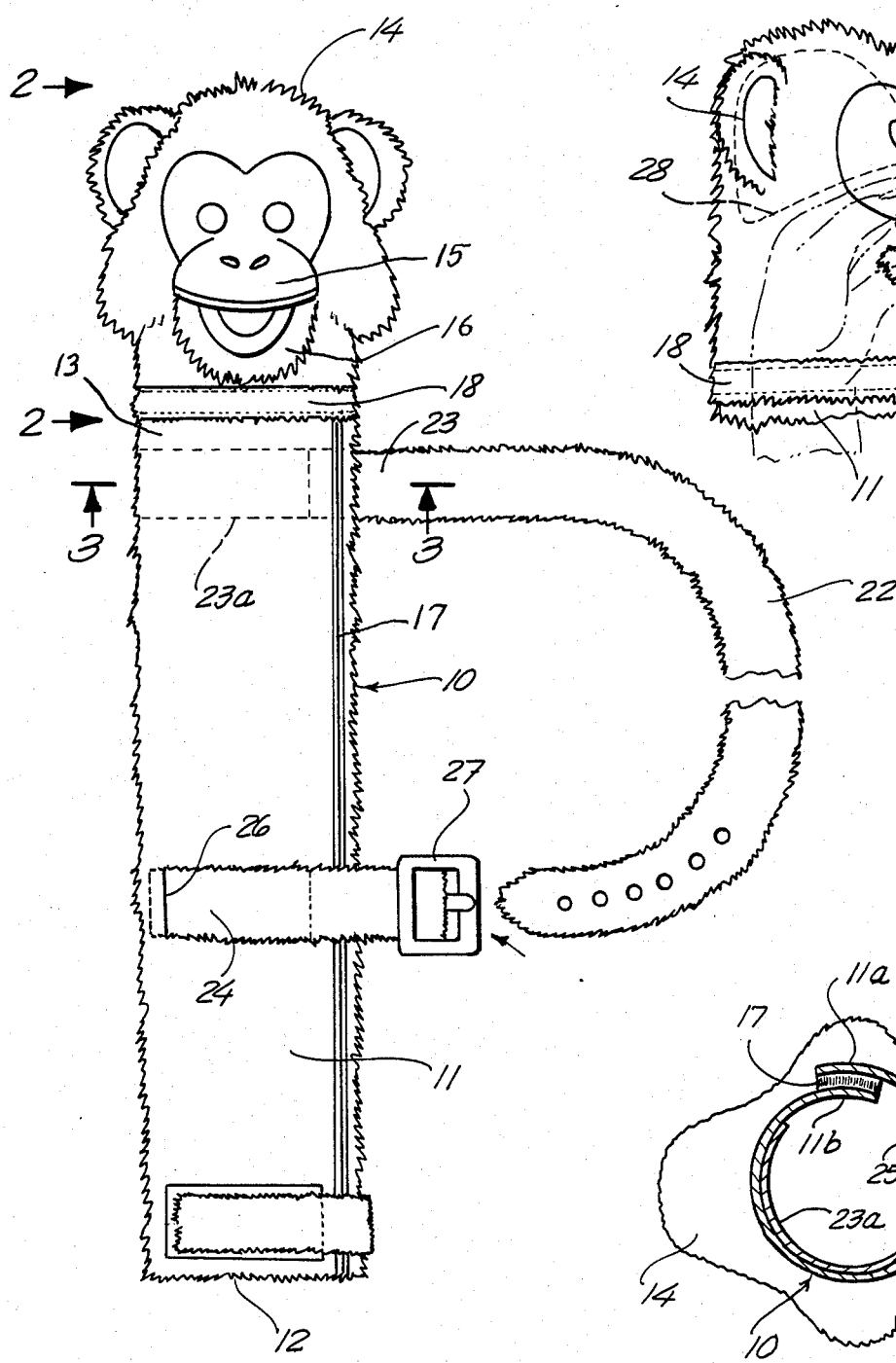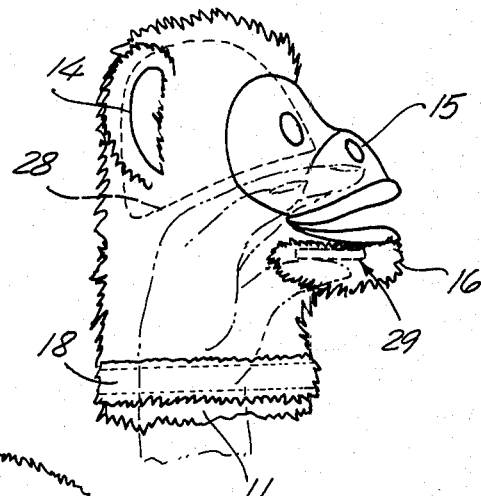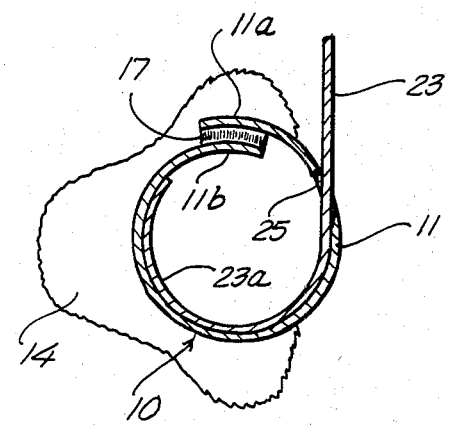

COMBINATION SLING AND THERAPY DEVICE

This invention relates to a combination sling and therapy device in the form of an elongated tubular member of pliable material, open at one end and closed at the other end, and having a slit portion extending throughout the major portion of its length incorporating adjustable fastener means whereby the tubular member can closely envelop an arm and cast assemblage from a point adjacent the fingers to at least the elbow of the user, an elongated band member having opposed ends engaging spaced portions of the tubular member, said band member being of a length to extend over the shoulder of a user and having adjustable means for providing the desired angular support for the forearm and cast, the closed end of said tubular member having a puppet-like characterization in which protruding movable lip portions are positioned to receive the thumb and fingers of the user, and at least one of said lip portions having a pressure actuated sound device for encouraging periodic manipulation of the thumb and fingers.

Broken arms, as frequently encountered in children of all ages, present a special problem in that the restraining effect of a cast needed to support the bone during the healing process tends to encourage complete immobility of the afflicted limb. This can have a seriously debilitating effect on the afflicted limb which can persist long after the cast has been removed.

In many fracture situations the supportive cast leaves the fingers and thumb free to move, and frequent manipulation of the thumb and fingers can keep up muscle tone and minimize such debilitating effect. The problem, however, is that it is difficult with all children, and almost impossible with the very young, to induce sufficient finger manipulation to provide a meaningful beneficial effect.

To overcome this problem a primary object of the present invention is to provide a sling having visible and audible means for encouraging finger manipulation, so the sling can also function as a therapy device. Basically the combination sling and therapy device incorporates, as an integral and properly positioned part of the sling, a puppet-like characterization having movable lip portions to receive the thumb and fingers of the user, with at least one of the lip portions containing a sound device activated by the application of pressure between the thumb and fingers.

A preliminary patent search revealed considerable activity in the puppet art, and considerable activity in the sling art; but no prior patent was encountered which was considered to suggest the unique combination of the present invention.

One adaptation of the combination sling and therapy device can be produced in two mirror-image forms to accommodate either a left or right afflicted arm. Another adaptation of the device has a novel supporting, over-the-shoulder band construction which permits one device to be used on either the left or right arm. Either adaptation of the device will be provided in a plurality of sizes to accommodate children of different age and size.

In the first adaptation of the device a puppet-like head is joined, suitably at a collar portion, to an elongated fabric member having "Velcro" or other adjustable fastener means along edges adapted to overlap at the upper side of the engaged arm so as to form a tubular member closely enveloping the arm and cast assemblage. In the second adaptation above-mentioned the edges of the elongated fabric member may meet centrally of the side of the device facing the user, and may be joined together by separable fastener or other joining means.

The puppet-like head can be of widely varied characterization but should have protruding movable lips into which the thumb and fingers of the user can extend; and these lips are oriented to extend toward the body of the user. This orientation will naturally receive the thumb and fingers in the normal configuration of a cast enveloped arm as held against the body of the afflicted individual.

The fabric forming the tubular member is preferably of an open-weave, two-way stretch variety to permit "breathing" and to facilitate a close, contour conforming fit around the arm and cast assemblage. The combination of the adjustable "Velcro" fasteners and the two-way stretch fabric will permit a device of particular size to accommodate a substantial variation in the size of the arm and cast assemblage.

It is also contemplated that the device be produced in two types, one extending to the elbow to encase a lower arm cast, and a longer type suitable to encase a cast which extends onto the upper arm.

In the latter instance the free end of the tubular member is preferably provided with an adjustable circumferential fastener to afford proper, non-slipping support on the upper arm of the user.

To provide the desired angular support of the arm-cast assemblage, the device is provided with an elongated band member adapted to extend over the shoulder of the user and having adjustable means for providing the desired length. In a device adapted for only left or right arm use, one end of the band member is attached to a portion of the tubular member at a position remote from the body of the user, and adjacent the puppet-like head. The other end joins the tubular member at a position adjacent the body of the user, and at approximately the elbow portion of the arm-cast assemblage. The adjustable means, which can suitably be of the belt-buckle or the "Velcro" fastener type is preferably located near the last named end of the band, and thus disposed at the back of the user.

In the "universal" type device, which can be used with either the left or right arm, the band member is interchangeably joined to the device at diametrically spaced points adjacent the elbow portion. The other end can be similarly interchangeably joined to the device adjacent the wrist portion, or alternatively said end can terminate in a loop which loosely encircles the wrist portion. The interchangeable joining of an end of the band member to the tubular member may be accomplished by an arcuate template fitting within the tubular member and having on the convex surface a projecting loop which passes outwardly through one of two slits in the tubular member, i.e. the slit that will be on the upper side of the device on the afflicted arm. The band end is then passed through the loop of the template and secured, via button, "Velcro" fastener, or the like to the main body of the band. Means is also provided in the band member to adjust its length to the size of the particular user.

The presence and location of the puppet-like head will, by itself, provide some inducement for finger manipulation, particularly among younger children. The inducement is enhanced, however, by providing a sound device in one of the lip portions which is activated by the application of pressure between the thumb (in the lower lip) and the fingers (in the upper lip).

The type of sound device can be widely varied. For the very young a single snap or squeak sound will suffice. For children who are somewhat older, for example early scouting age, a two pitch sound device would be desirable. With a two pitch device the child could be encouraged to practice and master the Morse Code, meanwhile benefitting from the extensive finger manipulation. A still further possibility is to include a four tone sound device, preferably in the upper lip, which will be responsive to application of pressure between the thumb and individual fingers.

The fabric of the tubular member suitably has an outer looped or otherwise napped surface; and for the optimum in aesthetic effect will be selected to have a color and texture simulating an extension of the puppet-like head. Also for aesthetic effect the over-the-shoulder band can suitably be fashioned from, or covered with, the fabric used in the tubular member.

As the combination sling and therapy device will inherently be used for several weeks, depending on the bonehealing time, it is important that all materials used in the device be of a type which will withstand periodic laundering.

Novel features of the combination sling and therapy device of the present invention will be more fully understood from a consideration of the following description having reference to the accompanying drawing in which various parts of the device are identified by suitable reference characters in each of the views, and in which:

FIG. 1 is an extended face view of the device as it might be seen when lying on a horizontal surface.

FIG. 2 is a fragmentary view of the device as shown in FIG. 1 taken in the direction of the arrows 2—2.

FIG. 3 is a sectional view substantially on the line 3—3 of FIG. 1.

Figure 4:
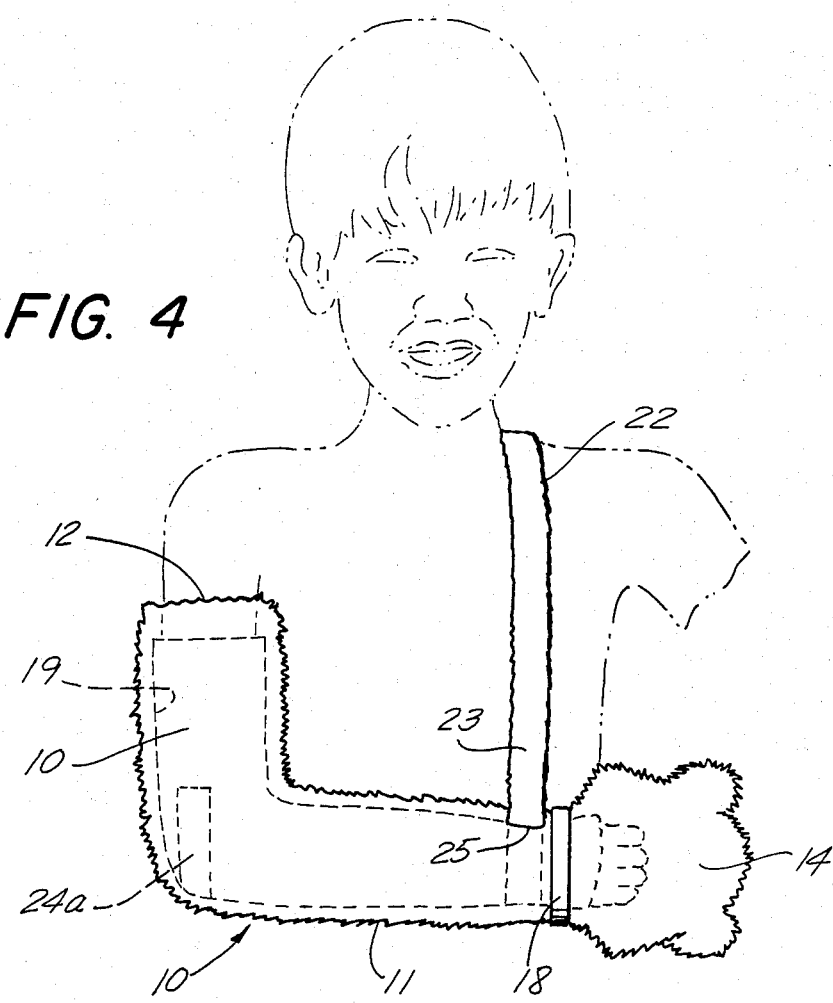
FIG. 4 is a front view of the device showing the configuration it would assume as to the arm of a wearer.

As shown in FIGS. 1 to 6 of the drawing the combination sling and therapy device 10 comprises an elongated tubular member 11 open at end 12 to receive an arm and closed at end 13 by a puppet-like head 14 having forwardly protruding and movable upper and lower lip portions 15 and 16 respectively. The lip portions are of hollowed construction to freely receive the fingers (in the upper lip) and thumb (in the lower lip) as clearly indicated in FIG. 2.

Figure 6:
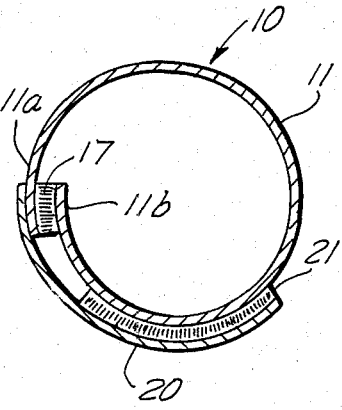
FIG. 6 is a sectional view substantially on the line 6—6 of FIG. 5.

The tubular member 11 is formed of a sheet of fabric having a width slightly greater than the circumference of the arm and cast to be accommodated to provide overlapping edges 11a, 11b as seen in FIGS. 3 and 6 on which are mounted interengaging elements of a "Velcro" fastener 17. It will be apparent that the "Velcro" fastener permits limited variation in the circumferential dimension of the tubular member 11 at different positions along its length to enable close fitting of the device to an engaged arm and cast.

Figure 5:
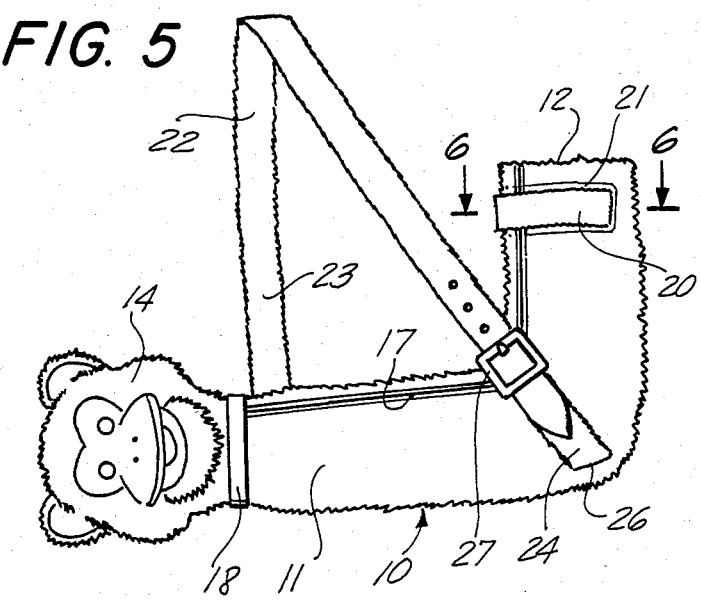
FIG. 5 is a view of the reverse side of the device as shown in FIG. 4 with the outline of the wearer omitted.

The sheet of material forming the tubular member 11 is joined to the puppet-like head 14 in the region of the collar 18 and oriented in a manner to dispose the overlapped edges 11a, 11b in the upper side of the device when mounted on a wearer as seen in FIG. 5. This means that for support of a right arm the overlapped edges 11a, 11b will be at the right side of the puppet-like head 14; whereas to accommodate a left arm the overlapped edges 11a, 11b would be at the left side of the puppet-like head and all parts of the assemblage would be oriented as the mirror image of the showing in FIG. 1.

As clearly shown in FIGS. 4 and 5 the tubular member 11 is of a length to extend around the elbow and onto the upper arm to a point close to the armpit of the intended wearer so as to envelope any arm cast normally encountered, including those in which the cast 19, as shown in FIG. 4, extends onto the upper arm. Adjacent its open end 12 the outer overlapping edge 11a of the tubular member 11 is provided with a circumferential extension 20 adjustably secured to the member 11 by elements of a "Velcro" fastener 21 as seen in FIG. 6. The adjustment provided by the circumferential extension 20 and "Velcro" fastener 21 permits easy circumferential adjustment of the tubular member 11 to prevent its downward slipping on the arm of the wearer.

Proper orientation of the engaged and supprted arm in cast is provided by an over-the-shoulder strap 22 with one end 23 secured to the tubular member 11 at the outer side of the wrist portion and the other end 24 secured to the tubular member 11 at the inner side of the elbow portion. The end 23 passes through a slit 25 in the tubular member 11 with the portion 23a extending inside the tubular member being stitched or otherwise secured to the tubular member through a major portion of its circumference as shown in FIG. 3. Similarly, the end 24 passes through a slit 26 at the lower elbow portion of the tubular member and the inwardly extending portion 24a is stitched or otherwise secured in angular orientation to the inner surface of the tubular member 11 as shown in FIG. 4.

Adjustable means is provided in the strap 22 adjacent the end 24 thereof as indicated by the buckle 27 for properly adjusting the length of the strap 22 to the size of the particular user. It will be understood in this connection that any type of adjustable means may be provided, and that maximum means of adjustment would be provided by employing "Velcro" fastener elements between overlapped portions of the strap 22.

The particular characterization of the puppet like head 14 is given merely for purpose of illustration, and it will be understood that any ornamental characterization can be provided in the head 14 so long as it incorporates protruding upper and lower lip portions 15 and 16 of a size to accommodate the fingers and thumb respectively of the user. Depending upon the configuration of the head 14, an appropriate filler and shaping insert 28 will be provided to maintain the desired head contour as is conventional in the puppet art. Such insert, however, should preferably be of a type to withstand laundering, or be readily removable during laundering.

In at least one of the lip portions 15, 16 a sound producing device 29 is incorporated as diagramatically indicated in FIG. 2 and is positioned in such a way as to be activated by application of a significant amount of pressure between the thumb and fingers. With the purpose of the sound device being to stimulate significant finger manipulation on the part of the particular user, it will be apparent that selection of the type sound device to incorporate will depend on the age of the intended user. The variations to be taken into account include in particular the amount of pressure needed to activate, and the type of sound being emitted.

For very young users a device emitting a single sound with application of relatively little pressure will be appropriate. For users in the 3 to 5 year age bracket a device requiring substantially greater application of pressure should be used in order to provide the desired therapeutic benefit. For users 6 years of age or older, it would even be desirable to include a device emitting variable sounds in response to individual finger movements applied against thumb pressure as a means to stimulate a continuing interest in using the device for its intended therapeutic purpose. It will be understood in this connection that when employing sound emitting inserts adapted to generate different or variable sounds it is within the scope of the invention to mount such inserts in either the upper or lower lip portion of the puppet like head.

The tubular member 11 and the strap 12 are suitably fashioned from fabric having a fairly open or "breathing" structure and preferably having limited two-way stretch characteristics. From the standpoint of aesthetic appeal, the fabric can suitably be looped or otherwise napped on its outer surface, with color and texture being selected to match or compliment the material used in fashioning the puppet like head.

The material selected should be of a durable nature, realizing that the device may be used for several weeks or months and should be of a type to permit frequent laundering.

Figure 7:
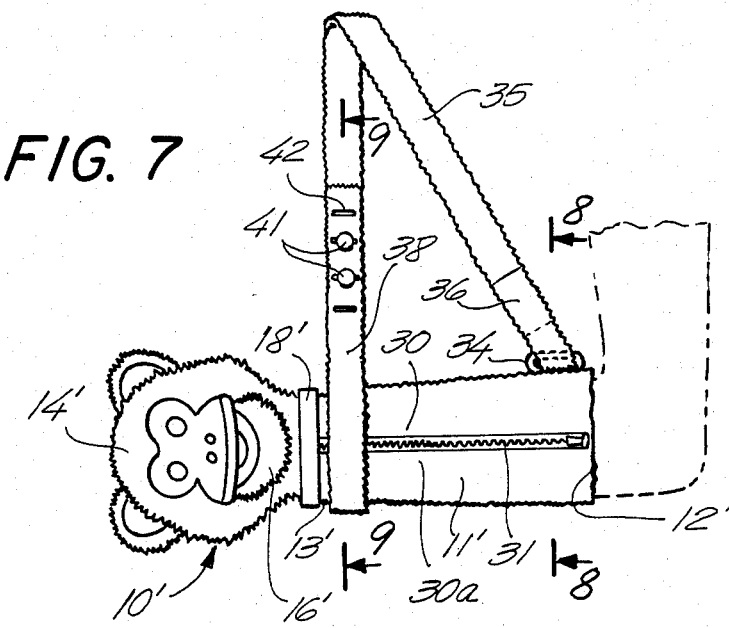
FIG. 7 is a view similar to FIG. 5 showing a modified "universal" form of construction.
Figure 8:
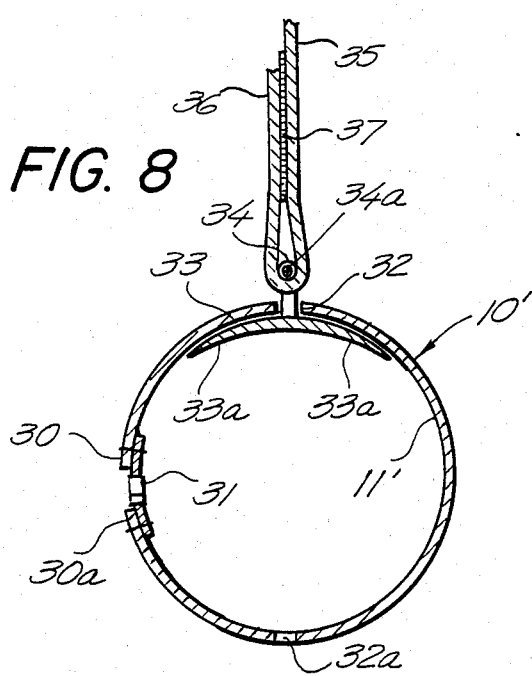
FIG. 8 is a sectional view substantially on the line 8—8 of FIG. 7.
Figure 9:
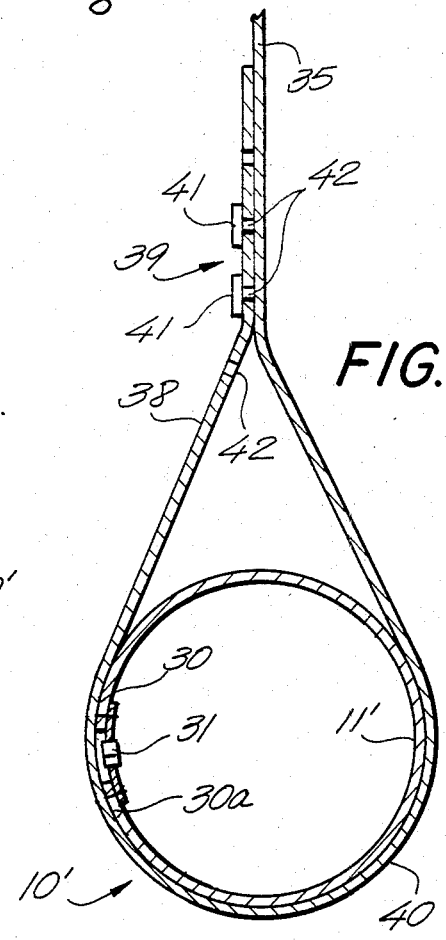
FIG. 9 is a sectional view substantially on the line 9—9 of FIG. 7.

FIGS. 7, 8 and 9 illustrate what might be termed a "universal" adaptation of the invention wherein a single form of the device is adapted for use on either a left arm or a right arm. The device as shown in FIGS. 7, 8 and 9 is of a shorter variety adapted for use with a wrist or hand cast; but it is to be understood that the modifications shown in FIGS. 7, 8 and 9 are equally applicable to the longer type device shown in FIGS. 1 to 6 and adapted to extend around the elbow and onto the upper arm of the user.

For ease of cross reference, like parts of the device will be identified by "primed forms" of the reference characters previously employed. Thus the device 10' comprises a tubular fabric member 11' having an open end 12' and a closed end 13' joined to a puppet like head 14' suitably at a collar portion 18'.

The puppet like head 14' is oriented to face the body of the wearer when the device is in use, and the tubular member 11' is longitudinally slit to provide edges 30,30a joined by suitable fastener means, such as the separable fastener 31 which is centrally of the body side of the device and substantially aligned with lower lip 16' of the puppet like head.

For interchangeably using the device 10' on either a right or left arm, the tubular member 11 is provided, adjacent the elbow portion of the device, with diametrically opposed slits 32, 32a as clearly shown in FIG. 8, each spaced approximately 90° from the fastener means 31. The slits 32,32a are interchangeably engaged by an arcuate template generally conforming to the curvature of the tubular member as mounted on an arm and having an elongated loop 34 which protrudes through the aligned slit 32 or 32a. An over the shoulder strap 35 has an end 36 which is passed through the loop 34 and adjustably secured to the strap 35 by a "Velcro" fastener 37.

As shown in FIGS. 7 and 8, with the arcuate template 33 engaged with slit 32, the device is intended for application to the right arm of the user. For use on the left arm, the strap 35 and template 34 are simply disengaged and reassembled with the template extending through slit 32a. It will be understood in this connection that the wrist end of the device can be supported, if desired, by providing diagrammatically opposed slits comparable to the slits 32,32a adjacent the collar 18' and employing a second arcuate template 33 for detachable and adjustable engagement of the over the shoulder strap 35.

FIGS. 7 and 9 illustrate an alternative way of supporting the wrist end of the device wherein the end 38 of the over the shoulder strap is passed around the arm and secured to the body of the strap 35 by adjustable fastener means 39 to form a loop 40 which effectively cradles and supports the wrist portion of the assemblage when in use. For purpose of illustration the fastener means 39 has been shown as comprising buttons 41 on the strap 35 adjustably engaging a plurality of button holes 42 in the strap end 38. It will be understood, however, that any adjustable fastening means can be employed including, inter alia, a "Velcro" fastener or a belt buckle adjustment as shown in FIG. 1.

In providing the universal type device shown in FIGS. 7 to 9 the arcuate template 33 is considered ciritical in providing a quick and easy adaptation of the device to either left arm or right arm use. As shown in FIG. 8, the ends 33a of the template have been shown as slightly tapered to provide form fitting flexibility to the template which is suitably fashioned as a molded plastic part. Depending on the plastic used and in order to provide adequate strength, the loop portion 34 of the template can be reinforced, if desired, by a metal core 34a, or alternatively the loop 34 can comprise a separate metal part molded into the template 33.

While the universal form of the device has been described as having alternative means of support for the wrist end of the device, it is considered that selection of which type of support to use should be based, in part, on the age of the child for which the device is intended. For the very young, the use of the spaced slits 32,32a and template 33 at the wrist end of the device would be preferable. For somewhat older children, however, the loop support shown in FIGS. 7 and 9 has the advantage of providing somewhat greater freedom of use of the afflicted arm.

It goes without saying that the universal form of the device provides the economic advantage of eliminating the need of maintaining a double inventory to cover the unpredictability in occurrence of left arm and right arm fractures.

Various changes and modifications in the combination sling and therapy device as herein disclosed may occur to those skilled in the art. To the extent that such changes and modifications are embraced by the appended claims, it is to be understood that they are embraced by the present invention.

I claim:

1. A combination sling and therapy device comprising an elongated tubular member of pliable material, open at one end and closed at the other end, and having a slit portion extending throughout the major portion of its length incorporating adjustable fastener means whereby the tubular member can closely envelop an arm and cast assemblage from a point adjacent the fingers to at least the elbow of the user, an elongated band member having opposed ends engaging spaced portions of the tubular member, said band member being of a length to extend over the shoulder of a user and having adjustable means for providing the desired angular support for the forearm and cast, the closed end of said tubular member having a puppet-like characterization in which protruding movable lip portions are positioned to receive the thumb and fingers of the user, and at least one of said lip portions having a pressure actuated sound device for encouraging periodic manipulation of the thumb and fingers.

2. A combination sling and therapy device as defined in claim 1, wherein the device is fashioned in one of two mirror-image configurations for respective right arm and left arm use, the slit portion being positioned to be above the supported arm, and the movable lip portions of the puppet-like characterization protruding in the direction of the body of the user.

3. A combination sling and therapy device as defined in claim 2, wherein one end of the band member joins the tubular member at a point adjacent the puppet-like characterization and at a portion of the tubular member remote from the body of the user, and the other end of said band joins the tubular member at a portion of the tubular member adjacent the body at approximately the location of the elbow of the user.

4. A combination sling and therapy device as defined in claim 1, wherein the device is of "universal" form, fitting either left or right arms, the slit portion being centrally of the side of the device facing the user, and the band member having interchangeable engagement with the tubular member at the elbow portion and wrist portion of the device.

5. A combination sling and therapy device as defined in claim 4, wherein the tubular member has, at least at the elbow portion, opposed elongated apertures spaced about 90° from said slit portion, and the device being adapted selectively for right arm or left arm use by passing said band member through the loop portion of an arcuate template protruding through the aperture which will be at the upper side of the selected arm.

6. A combination sling and therapy device as defined in claim 5, wherein said opposed apertures for interchangeably receiving looped portions of arcuate templates are located at both the wrist portion and elbow portion of the device.

7. A combination sling and therapy device as defined in claim 5, wherein said band member engages the looped portion of an arcuate template at only the elbow portion of the device, and the other end of the band member forms an adjustable closed looped adapted to encircle and cradle the wrist portion of the arm and cast assemblage.

8. A combination sling and therapy device as defined in claim 7, wherein the last named end of said band member incorporates adjustable fastener means adapted simultaneously to form said closed loop and to adjust the length of said band member to provide the proper angular support of the arm and case assemblage.

9. A combination sling and therapy device as defined in claim 1, wherein the tubular member extends beyond the elbow to the upper arm, and interengaging means is provided at the open end of the tubular member for adjustably conforming the circumference of the said open end to the upper arm of the user.

10. A combination sling and therapy device as defined in claim 1, wherein the tubular member is a separate part joined to said puppet-like characterization at a collar portion, said tubular member being fashioned from a fabric having a relatively open weave providing two-way stretch characteristics.

11. A combination sling and therapy device as defined in claim 8, wherein the fabric of said tubular member provides an external napped surface.

12. A combination sling and therapy device as defined in claim 8, wherein the fabric of said tubular member provides an external napped surface, and the nature and color of said napped surface are such as to simulate an extension of the puppet-like characterization.

13. A combination sling and therapy device as defined in claim 1 as adapted for very young children, said device being characterized as having in one of the lip portions a sound device emitting a single sound when actuated by pressure between the thumb and fingers.

14. A combination sling and therapy device as defined in claim 1 as adapted for older children and characterized as having in one of the lip portions a sound device emitting a plurality of sounds upon application of pressure between the thumb and individual opposed fingers.

15. A combination sling and therapy device as defined in claim 1, wherein all parts of the device are fashioned from materials capable of withstanding repeated laundering.

* * * * *